(12) United States Patent
Stepp et al.

(10) Patent No.: US 11,490,816 B2
(45) Date of Patent: Nov. 8, 2022

(54) APPARATUS AND METHOD FOR FLUORESCENCE MEASUREMENTS ON TISSUE FOR THE DETERMINATION OF BLOOD FLUOROPHORES

(71) Applicants: Herbert Stepp, Planegg (DE); Georg Hennig, Munich (DE); Christian Homann, Munich (DE)

(72) Inventors: Herbert Stepp, Planegg (DE); Georg Hennig, Munich (DE); Christian Homann, Munich (DE); Gary M. Brittenham, New York, NY (US); Michael Grossman, Munich (DE)

(73) Assignee: FerroSens GmbH, Munich (DE)

( * ) Notice: Subject to any disclaimer, the term of this patent is extended or adjusted under 35 U.S.C. 154(b) by 622 days.

(21) Appl. No.: 15/551,303

(22) PCT Filed: Feb. 17, 2016

(86) PCT No.: PCT/EP2016/053389
§ 371 (c)(1),
(2) Date: Aug. 16, 2017

(87) PCT Pub. No.: WO2016/131886
PCT Pub. Date: Aug. 25, 2016

(65) Prior Publication Data
US 2018/0042482 A1 Feb. 15, 2018

Related U.S. Application Data

(60) Provisional application No. 62/201,449, filed on Aug. 5, 2015, provisional application No. 62/126,221, filed
(Continued)

(51) Int. Cl.
*A61B 5/1455* (2006.01)
*A61B 5/00* (2006.01)
(Continued)

(52) U.S. Cl.
CPC .......... *A61B 5/0071* (2013.01); *A61B 5/1455* (2013.01); *A61B 5/14546* (2013.01);
(Continued)

(58) Field of Classification Search
None
See application file for complete search history.

(56) References Cited

U.S. PATENT DOCUMENTS

| | | | | |
|---|---|---|---|---|
| 4,178,917 A | * | 12/1979 | Shapiro | A61B 5/0071 356/317 |
| 5,601,080 A | * | 2/1997 | Oppenheimer | G01N 21/532 356/39 |

(Continued)

FOREIGN PATENT DOCUMENTS

| CN | 103565410 B | 2/2014 |
|---|---|---|
| CN | 103930782 A | 7/2014 |

(Continued)

OTHER PUBLICATIONS

International Search Report issued in PCT/EP2016/053389, dated May 3, 2016.

(Continued)

*Primary Examiner* — Marjan Fardanesh
(74) *Attorney, Agent, or Firm* — Medler Ferro Woodhouse & Mills

(57) ABSTRACT

The present invention is directed to an apparatus (10) for reliable quantitative measurement of a fluorescent blood analyte in tissue (12) comprising: at least one light source (14), the light source (14) emitting excitation light at least at a first wavelength range between 350 nm and 450 nm to the tissue (12); a detection unit (16), the detection unit (16) measuring: a) a portion of the fluorescent light emitted by the fluorescent blood analyte excited at the first wavelength range; and b) a portion of the auto fluorescence emitted by
(Continued)

the tissue (12); and/or c1) a portion of the remitted excitation light at the first wavelength range, and c2) a portion of the remitted light at a second wavelength range; and a control unit (18), the control unit (18) operating the light source (14) and detection unit (16). The present invention is further directed to a method for quantitative measurement of a fluorescent blood analyte in tissue (12).

25 Claims, 12 Drawing Sheets

Related U.S. Application Data on Feb. 27, 2015, provisional application No. 62/117,801, filed on Feb. 18, 2015.

(51) Int. Cl.
*G01N 21/31* (2006.01)
*G01N 21/49* (2006.01)
*G01N 21/64* (2006.01)
*A61B 5/145* (2006.01)

(52) U.S. Cl.
CPC ....... *A61B 5/14556* (2013.01); *G01N 21/314* (2013.01); *G01N 21/49* (2013.01); *G01N 21/6486* (2013.01)

(56) References Cited

U.S. PATENT DOCUMENTS

| | | |
|---|---|---|
| 2004/0010195 A1* | 1/2004 | Zelenchuk ........... A61B 5/0084 600/476 |
| 2014/0012104 A1 | 1/2014 | Chen et al. |
| 2014/0163387 A1 | 6/2014 | Kang et al. |
| 2014/0235973 A1 | 8/2014 | Brittenham et al. |

FOREIGN PATENT DOCUMENTS

| | | |
|---|---|---|
| EP | 0 003 015 | 7/1979 |
| WO | 2005/032361 | 4/2005 |
| WO | 2013/040398 | 3/2013 |

OTHER PUBLICATIONS

Henning, Georg et al., "Dual-wavelength excitation to reduce background fluorescence for fluorescence spectroscopic quantitation of erythrocyte zinc protoporphyrin-IX and protoporphyrin-IX from whole blood and oral mucosa," Progress in Biomedical Optics and Imaging, Spie—International Society for Optical Engineering, Bellingham, WA, US, vol. 8951, Feb. 28, 2014, pp. 89510J-8951J.

* cited by examiner

Calculated fluorescence intensity

Calculated fluorescence intensity

APPARATUS AND METHOD FOR FLUORESCENCE MEASUREMENTS ON TISSUE FOR THE DETERMINATION OF BLOOD FLUOROPHORES

CROSS REFERENCE

This application claims priority to U.S. Provisional Patent Application Ser. No. 62/117,801 filed Feb. 18, 2015, U.S. Provisional Patent Application Ser. No. 62/126,221, filed Feb. 27, 2015, and U.S. Provisional Patent Application Ser. No. 62/201,449, filed Aug. 5, 2015, the contents of each of which are incorporated herein by reference thereto.

FIELD

The disclosed subject matter relates to a system for fluorescence and reflectance measurements. Particularly, the present disclosed subject matter is directed to the quantitative determination of blood and/or blood bound fluorophores.

BACKGROUND OF THE DISCLOSED SUBJECT MATTER

When measuring the fluorescence of a blood or blood-bound fluorophore, e.g., the red blood cell bound fluorophore zinc protoporphyrin, from tissue, e.g., the oral mucosa, the fluorescence intensity depends on the tissue structure and tissue optical properties. This may be problematic for achieving accurate measurements. Generally, the parameter with the largest influence is the amount of blood found in the tissue. There have been efforts to detect the amount of influence imposed by relevant parameters (tissue structure, tissue optical properties). These efforts include: extraction of a parameter quantifying the influence of tissue structure and tissue optical properties from the autofluorescence spectrum measured upon blue light excitation, and extraction of this parameter by measuring the amount of remitted light at the excitation wavelength and a second wavelength. There is a need to reliably measure the intensity of fluorescent light emitted from blood and/or blood bound fluorophores that takes account of the influences on measurements caused by the tissue structure and tissue optical properties.

Measuring the intensity of fluorescent light emitted from one or more blood and/or blood bound fluorophores is necessary for various diagnostic methods. A determination of the concentration of the fluorophores or the concentration relative to the absorbing heme or hemoglobin can be made from the intensity measurement. For example, measuring the concentration-ratio of erythrocyte-bound zinc protoporphyrin (ZnPP), and/or protoporphyrin IX (PP) to heme can be used for the diagnosis of iron deficiency, lead poisoning, and different porphyrias.

To determine the ZnPP and PP concentrations, blood is typically taken from the subject and fluorescence spectroscopic measurements are conducted, either directly on the blood sample or after separation of the fluorophores from the sample. In this way, ZnPP and PP can be separated and quantitatively determined by HPLC (high performance liquid chromatography). For direct measurements on a blood sample, the "hematofluorometer" (e.g., model 206D of the company AVIV Biomedical, Inc., Lakewood, N.J., USA) illuminates a drop of blood in vitro and estimates the ratio ZnPP/heme from the measured fluorescence intensity.

Alternatively, fluorescence spectroscopic measurements can be made on intact tissue in vivo. In a manner similar to the hematofluorometer, intact tissue (e.g., the oral mucosa) is illuminated with excitation light. The fluorescence intensity from the erythrocyte-bound ZnPP and PP is measured, and the ratio of ZnPP/heme and PP/heme can be derived from this measurement. In contrast to measurement from a blood sample, however, the precise structure of the tissue, e.g., thickness of the epithelium which does not contain blood and does not contribute to the ZnPP fluorescence signal, and other tissue parameters are unknown. These tissue parameters include tissue absorption, scattering, blood vessel diameter and the blood volume fraction (BVF), which is the relative proportion of the blood volume to the tissue volume. These tissue parameters can substantially influence the fluorescence intensity value, especially at low BVF. As a consequence, the measured intensity of the fluorescent light varies in an unknown, intra- and inter-individual way. Consequently, if the desired values (the ratios ZnPP/heme and PP/heme) are derived from the measured fluorescence signal, these values will also be influenced by this unknown variation. In principle, determination of the tissue parameters is possible, for example, by white light reflectance measurements but such measurements are complicated, expensive, and have uncertain effectiveness.

SUMMARY

As described and embodied herein, an apparatus and method is provided to overcome the problems of inaccurate measurement of a blood analyte in tissue. The apparatus and method reliably measures the blood analyte. The invention is directed to an apparatus for reliable quantitative measurement of a fluorescent blood analyte in tissue comprising the features of claim 1 and a method for a quantitative measurement of a fluorescent blood analyte in tissue with the features of claim 19. Advantageous configurations of the apparatus and the method are also apparent from the respectively dependent claims.

In accordance with one aspect of the described subject matter, an apparatus is provided for measurement of a blood analyte in tissue comprising: At least one light source, the light source emitting excitation light at least at a first wavelength range between 350 nm and 450 nm to the tissue, a detection unit, the detection unit measuring: a) a portion of the fluorescent light emitted by the fluorescent blood analyte excited at the first wavelength range; and b) a portion of the autofluorescence emitted by the tissue; and/or c1) a portion of the remitted excitation light at the first wavelength range, and c2) a portion of the remitted light at a second wavelength range. The apparatus further includes a control unit, the control unit operating the light source and detection unit. Since the tissue autofluorescence is partially absorbed by the blood before it reaches the detector, the autofluorescence can serve as a measure of the amount of blood in the tissue volume, the blood volume fraction (BVF), as well as other tissue parameters. Therefore, this measure can serve for excluding measurements unsuitable for reliable quantitative determination of the fluorescent blood analyte. Further, remission, the propagation of light back from tissue toward the light source, includes both the light reflected from the tissue surface and the light scattered within the tissue that then passes through the tissue surface back to the source. Light at the excitation wavelength is strongly absorbed by blood so that the amount of remitted light strongly depends on the BVF, while light in another wavelength range is less influenced by blood and the amount of remitted light therefore mainly depends on light scattering and epithelium layer thickness. Therefore, both measurements can be combined to derive a parameter identifying measurements and/or tissue sites suitable for quantitative fluorescence measurements of the blood analyte. Further, it is possible to use only the detected intensity of the remitted excitation light at the first wavelength range or the detected intensity of the remitted excitation light at the second wavelength range to derive a parameter identifying measurements and/or tissue sites suitable for quantitative fluorescence measurements of the blood analyte. With the described apparatus, locations at a tissue site can be identified where the thickness of the epithelial layer, the blood volume fraction, and other parameters of the tissue, are suitable to allow for quantitative evaluation of the measured analyte fluorescence.

In some embodiments, the apparatus comprises a processor configured to configured to determine a parameter from at least one intensity of said portion of the autofluorescence emitted by the tissue at a wavelength range between about 530 and 600 nm, especially about 580 nm, to identify measurements and/or tissue sites, where the detected amount of fluorescence light is a quantitative measure of the fluorescent blood analyte. Further, it is possible that the processor is configured or is additionally configured to derive a correction factor based on at least one intensity of said portion of the autofluorescence emitted by the tissue at a wavelength range between about 530 and 600 nm, especially about 580 nm, which allows scaling the measured fluorescence intensity, so that it is a quantitative measure of the fluorescent blood analyte. A wavelength range between about 530 and 600 nm means that the wavelength could be at 530 nm, 531 nm, 532 nm, 533 nm, 534 nm, 535 nm, 536 nm, 537 nm, 538 nm, 539 nm, 540 nm, 541 nm, 542 nm, 543 nm, 544 nm, 545 nm, 546 nm, 547 nm, 548 nm, 549 nm, 550 nm, 551 nm, 552 nm, 553 nm, 554 nm, 555 nm, 556 nm, 557 nm, 558 nm, 559 nm, 560 nm, 561 nm, 562 nm, 563 nm, 564 nm, 565 nm, 566 nm, 567 nm, 568 nm, 569 nm, 570 nm, 571 nm, 572 nm, 573 nm, 574 nm, 575 nm, 576 nm, 577 nm, 578 nm, 579 nm, 580 nm, 581 nm, 582 nm, 583 nm, 584 nm, 585 nm, 586 nm, 587 nm, 588 nm, 589 nm, 590 nm, 591 nm, 592 nm, 593 nm, 594 nm, 595 nm, 596 nm, 597 nm, 598 nm, 599 nm, 600 nm. As an example, the autofluorescence emitted by the tissue at a wavelength of 545 nm and/or 576 nm could be measured.

Further, it is possible that the processor is configured or is additionally configured to determine a parameter from the remitted light at the first wavelength range and the second wavelength range to identify measurements and/or tissue sites, where the detected amount of fluorescence light is a quantitative measure of the blood analyte. Further, it is possible that the processor is configured or is additionally configured to derive a correction factor from the remitted light at the first wavelength range and the second wavelength range, which allows for scaling the measured fluorescence intensity, so that it is a quantitative measure of the blood analyte. The ratio of a portion of the remitted excitation light at the first wavelength range ($R_1$) and a portion of the remitted light at a second wavelength range ($R_2$) could be corrected by a factor which is specific for the construction of the apparatus used. For example, the ratio $R_1/R_2$ could be corrected as $R_1^{0.8}/R_2$ with 0.8 as the correction factor specified for the apparatus. Another function of $R_1$ and $R_2$, containing correction factors specific for the apparatus could be applied as well.

In some embodiments, the second wavelength range is between 450 nm and 750 nm. This means that the second wavelength could be at 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm. Other wavelengths within the mention range are possible. Further, the first wavelength could be at 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, 400 nm, 401 nm, 402 nm, 403 nm, 404 nm, 405 nm, 406 nm, 407 nm, 408 nm, 409 nm, 410 nm, 411 nm, 412 nm, 413 nm, 414 nm, 415 nm, 416 nm, 417 nm, 418 nm, 419 nm, 420 nm, 421 nm, 422 nm, 423 nm, 424 nm, 425 nm, 426 nm, 427 nm, 428 nm, 429 nm, 430 nm, 431 nm, 432 nm, 433 nm, 434 nm, 435 nm, 436 nm, 437 nm, 438 nm, 439 nm, 440 nm, 441 nm, 442 nm, 443 nm, 444 nm, 445 nm, 446 nm, 447 nm, 448 nm, 449 nm or 450 nm. Additionally, the light source and detection unit can be configured as a single integral component. Other components of the inventive apparatus can also be part of the single integral component.

In some embodiments, the detection unit comprises optical means for collecting emitted fluorescent light and/or remitted light at the first and/or second wavelength ranges. Further, it is possible that the detection unit comprises a probe having a proximal end and a distal end, wherein the distal end is configured to be applied directly or indirectly to the tissue. In another embodiment the detection unit is configured as a probe having a proximal end and a distal end, wherein the distal end is configured to be applied directly or indirectly to the tissue. Furthermore, the probe could be designed to comprise at least one suction means formed at the distal end of the probe. Said suction means could comprise at least one suction aperture formed at the distal end of the probe. In yet another embodiment of the invention said probe comprises a cover attached to the distal end wherein the cover is configured to be applied directly or indirectly to the tissue. The at least one suction means could be formed within the cover. In a further embodiment, at least the detection unit is configured as a handheld device.

In some embodiments, the apparatus comprises a light guide guiding excitation light to the tissue and/or collecting emitted fluorescent light and/or remitted light at the first and/or second wavelength ranges. According to one embodiment of the apparatus, the light guide is an optical fiber or fiber bundle.

In certain embodiments, the measured fluorescent blood analyte includes the zinc protoporphyrin (ZnPP)/heme and/or protoporphyrin IX (PP)/heme ratios and/or ZnPP and/or PP concentrations. In some embodiments the apparatus is adapted to estimate the BVF.

In accordance with another aspect of the invention, a method is provided for measuring a blood analyte in tissue comprising the steps of: emitting excitation light at least at a first wavelength range between 350 nm and 450 nm to the tissue; and further a) detecting a portion of the fluorescent light emitted by the fluorescent blood analyte excited at the first wavelength range, and b) detecting a portion of the autofluorescence emitted by the tissue; and/or c1) detecting a portion of the remitted excitation light at the first wavelength range, and c2) detecting a portion of the remitted light at a second wavelength range; and determining an information for excluding measurements and/or tissue sites unsuitable for reliable quantitative determination of the fluorescent blood analyte based on at least one intensity of said autofluorescence portion emitted by the tissue at a wavelength range between about 530 and 600 nm, especially about 580 nm, and/or based on a parameter such as the ratio of the detected intensity of the remitted excitation light at the first wavelength range to the detected intensity of the remitted light at the second wavelength range or vice versa. Since the tissue autofluorescence is partially absorbed by the blood before it reaches the detector, the autofluorescence can serve as a measure of the amount of blood in the tissue volume, the blood volume fraction (BVF), as well as other tissue properties. Therefore, this measure serves for excluding measurements and/or tissue sites unsuitable for reliable determination of the fluorescent blood analyte concentration. A wavelength range between about 530 and 600 nm means that the wavelength could be at 530 nm, 531 nm, 532 nm, 533 nm, 534 nm, 535 nm, 536 nm, 537 nm, 538 nm, 539 nm, 540 nm, 541 nm, 542 nm, 543 nm, 544 nm, 545 nm, 546 nm, 547 nm, 548 nm, 549 nm, 550 nm, 551 nm, 552 nm, 553 nm, 554 nm, 555 nm, 556 nm, 557 nm, 558 nm, 559 nm, 560 nm, 561 nm, 562 nm, 563 nm, 564 nm, 565 nm, 566 nm, 567 nm, 568 nm, 569 nm, 570 nm, 571 nm, 572 nm, 573 nm, 574 nm, 575 nm, 576 nm, 577 nm, 578 nm, 579 nm, 580 nm, 581 nm, 582 nm, 583 nm, 584 nm, 585 nm, 586 nm, 587 nm, 588 nm, 589 nm, 590 nm, 591 nm, 592 nm, 593 nm, 594 nm, 595 nm, 596 nm, 597 nm, 598 nm, 599 nm, 600 nm. As an example, the autofluorescence emitted by the tissue at a wavelength of 545 nm and/or 576 nm could be measured.

Further, it is possible to use only the detected intensity of the remitted excitation light at the first wavelength range or the detected intensity of the remitted light at the second wavelength range to derive a parameter identifying measurements and/or tissue sites suitable for quantitative fluorescence measurements of the blood analyte. Further, remission, the propagation of light back from tissue toward the detector, includes the light reflected from the tissue surface and/or the light scattered within the tissue that then passes through the tissue surface back to the source. The ratio of a portion of the remitted excitation light at the first wavelength range ($R_1$) and a portion of the remitted light at a second wavelength range ($R_2$) could be corrected by a factor which is specific for the construction of the apparatus used. For example, the ratio $R_1/R_2$ could corrected as $R_1^{0.8}/R_2$ with 0.8 as the correction factor specified for the apparatus. Another function of $R_1$ and $R_2$, containing correction factors specific for the apparatus could be applied as well.

In some embodiments, the second wavelength range is between 450 nm and 750 nm. This means that the second wavelength could be at 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm. Other wavelengths within the mention range are possible. Further, the first wavelength could be at 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, 400 nm, 401 nm, 402 nm, 403 nm, 404 nm, 405 nm, 406 nm, 407 nm, 408 nm, 409 nm, 410 nm, 411 nm, 412 nm, 413 nm, 414 nm, 415 nm, 416 nm, 417 nm, 418 nm, 419 nm, 420 nm, 421 nm, 422 nm, 423 nm, 424 nm, 425 nm, 426 nm, 427 nm, 428 nm, 429 nm, 430 nm, 431 nm, 432 nm, 433 nm, 434 nm, 435 nm, 436 nm, 437 nm, 438 nm, 439 nm, 440 nm, 441 nm, 442 nm, 443 nm, 444 nm, 445 nm, 446 nm, 447 nm, 448 nm, 449 nm or 450 nm.

With the described method, tissue sites can be identified where the thickness of the epithelial layer, the blood volume fraction, and the optical parameters of the tissue, are suitable to allow for quantitative evaluation of the measured analyte fluorescence.

In one embodiment, the quantitatively determined blood analyte is the ZnPP/heme ratio, and the first wavelength is in the range of 395 to 435 nm and the second wavelength is about 520 nm. The remitted light is used to identify tissue sites suitable for reliable fluorescence measurements and/or to correct the measured fluorescence intensity so that it is reliable measure of the ZnPP/heme ratio.

In another embodiment, the quantitatively determined blood analyte is the ZnPP/heme ratio, and the first wavelength is in the range of 395 to 435 nm. The tissue autofluorescence in the wavelength range of 560 to 600 nm is used to identify tissue sites suitable for reliable fluorescence measurements and/or to correct the measured fluorescence intensity so that it is reliable measure of the ZnPP/heme ratio.

In another embodiment, the quantitatively determined blood analyte is a vitamin, e.g. vitamin A (retinol), and the first wavelength is in the range of 350 to 400 nm. Remitted light and/or tissue autofluorescence is used to identify tissue sites suitable for reliable fluorescence measurements and/or to correct the measured fluorescence intensity so that it is reliable measure of said vitamin.

BRIEF DESCRIPTION OF THE DRAWINGS

The accompanying drawings, which are incorporated in and constitute part of this specification, are included to illustrate and provide a further understanding of the method and system of the disclosed subject matter. Together with the description, the drawings serve to explain the principles of the disclosed subject matter. It is to be understood that both the foregoing general description and the following detailed description are exemplary and are intended to provide further explanation of the disclosed subject matter claimed. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

Figure 1:
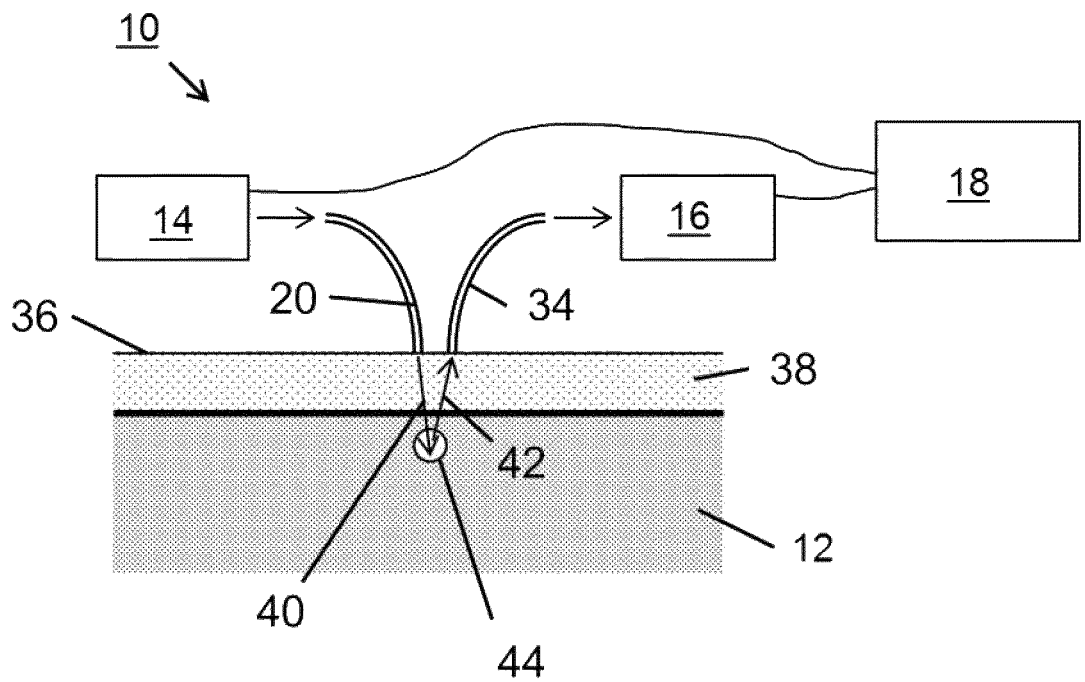
FIG. 1 is a schematic illustration of an apparatus according to one embodiment of the invention.

The apparatus and method described herein combines the fluorescence measurements of the analytes (for example, ZnPP or PP) with tissue autofluorescence and remission measurements. The two approaches, e.g., estimation of the BVF and epithelium thickness and other tissue parameters by using the tissue autofluorescence and estimation of optical parameters and epithelium thickness from remission measurements, may be combined to identify measurements done at inappropriate or appropriate tissue sites, or may be applied separately.

Since the tissue autofluorescence is partially absorbed by the blood before it reaches the detector, the autofluorescence can serve as a measure of the amount of blood in the tissue volume, the blood volume fraction (BVF), as well as other tissue parameters. If the undisturbed autofluorescence spectrum is unknown, the amount of autofluorescence photons absorbed by blood can be estimated by evaluating the minimum of autofluorescence found at the characteristic absorption maxima of blood (e.g., around 580 nm), relative to the total autofluorescence signal. In this manner, a parameter related to the true BVF and other tissue parameters can be derived. This parameter is here referred to as the "blood imprint". This can be done prior to the measurement to identify a suitable tissue site, during the measurements or after the measurement to exclude measurements which were done at tissue sites that are not suitable.

In some embodiments, remission can be used to determine the influence on the fluorescence intensity both (i) of tissue parameters including the BVF and, simultaneously, (ii) of the thickness of overlying scattering tissue layers. Remission, the propagation of light back from tissue toward the light source, includes the light reflected from the tissue surface and/or the light scattered within the tissue that then passes through the tissue surface back to the source. With the described measurement apparatus and method, locations at a tissue site can be identified where the thickness of the epithelial layer, the BVF, and other tissue parameters, are suitable to allow for quantitative evaluation of the measured analyte fluorescence. This can be done prior to the measurement to identify a suitable tissue site, during the measurements or after the measurement to exclude measurements which were done at tissue sites that are not suitable.

The blood imprint evaluated from the tissue autofluorescence and/or the result from the remission measurements can be used to exclude measurements from evaluation when the blood imprint is too small or too large and/or optical parameters are not suitable for a reliable quantitative determination of the analyte.

In another implementation, the tissue autofluorescence and/or remission measurements are monitored continuously, so that they can be used to assess the adequacy of the BVF and/or optical parameters prior to measurement of the analyte, and determine if the position of the measurement probe permits a reliable measurement (allowing appropriate repositioning the measurement probe). In general, the tissue autofluorescence and/or the remission measurements allow the calculation of a correction factor for the measured fluorescence intensity such that from the combination of the fluorescence intensity of the analyte and this correction factor, the concentration of the analyte can be estimated.

Referring to FIG. 1, an apparatus 10 and method for a reliable quantitative measurement of a fluorescent blood analyte in a tissue 12 are shown and described schematically. Light emitted by the excitation light source 14 is transported by an optical fiber 20 to the tissue surface 36. In the case of the determination of ZnPP and PP, for excitation, light in the blue spectral range is used, 395 to 435 nm, with a small spectral bandwidth. In this spectral range, blood absorption is at its maximum. The excitation light passes through the epithelium 38 before reaching the blood-perfused tissue 12. It should be noted that in tissue, typically, large amounts of light scatterers are found, so that a photon is normally scattered multiple times, changing the propagation direction of the photon. The light paths 40 and 42 therefore are sketched in a simplified way, not showing propagation direction changes. In the blood-perfused tissue 12, the excitation light may be absorbed by a blood fluorophore 44. A portion of the emitted fluorescent light is collected by an additional light guide 34 and is transferred to a detection unit 16 where it is detected. Light source 14 and detection unit 16 are controlled and read out by a control unit 18. The resulting measurements can be displayed in an indicator 46 (See FIG. 12). For ease of illustration, the light source 14 and the detection unit 16 are shown separately, but these can be combined in the same device. Optical fiber 20 and optical fiber 34 can also be identical so that excitation light is delivered to the tissue 12 by the same fiber that is used to detect the fluorescence light, with the light paths separated by a partially reflecting or dichroic mirror. The light source 14 may be used for fluorescence excitation, as well as for remission measurements. For the remission measurements, FIG. 1 sketches the measurement set-up as well, except that reference number 44 represents a scattering event of the (excitation) light and therefore only changes its propagation direction, but not its wavelength (as occurs during emission of fluorescent light).

The details of the evaluation of the remission and autofluorescence measurements to allow for identification of suitable tissue measurement sites are described herein.

Remission Measurements

For remission measurements, the light source 14 for fluorescence excitation is also able to emit, in addition to the excitation light, light at one or more further second wavelengths or wavelength ranges that are in a spectral range wherein the blood absorption is substantially smaller, for example in the green or red spectral range. The detection unit 16 measures not only the emitted fluorescent light, but, in addition, (i) the remitted part of the excitation light backscattered from the tissue 12, and (ii) backscattered light at the second wavelength. Overall, a complete measurement cycle would function in the following manner: first, the light source 14 emits excitation light, and the detection unit 16 measures fluorescent light emitted from the blood fluorophore 44. Second, the detection unit 16 measures the backscattered excitation light. Third, the light source 14 emits light at the second wavelength and the backscattered light is measured by the detection unit 16. Therefore, a total of at least three measurements are available: fluorescence intensity, intensity of the backscattered excitation light and intensity of the backscattered light at the second wavelength.

The measured fluorescence intensity depends, at least in part, on the epithelial layer thickness and the tissue optical parameters (scattering, absorption of the tissue). A fluorescence intensity too low for analyte measurement may be caused, for example, by (i) a large epithelial layer thickness (due to the distance of the fiber 20 from the blood-perfused tissue 12), (ii) excessive light scattering (due to the high proportion of remitted excitation light, which then is not available for fluorescence excitation), a (iii) low blood volume fraction (BVF) in tissue 12, or (iv) too large blood vessels (since fluorophores inside the large vessels are light-protected by surrounding absorbers in the blood). These confounding factors must be distinguished from a low fluorescence intensity due to a low fluorophore analyte concentration.

Figure 2:
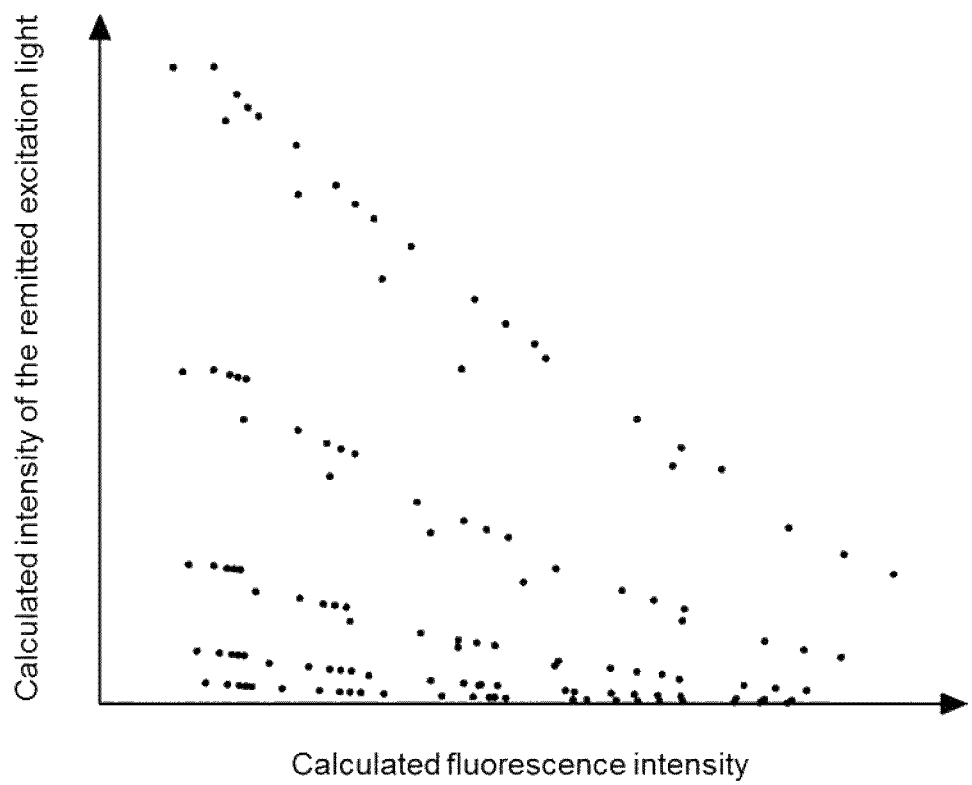
FIG. 2 is a graph showing the calculated intensity of the remitted excitation light plotted against the calculated fluorescence intensity for a Monte Carlo computer simulation.
Figure 3:
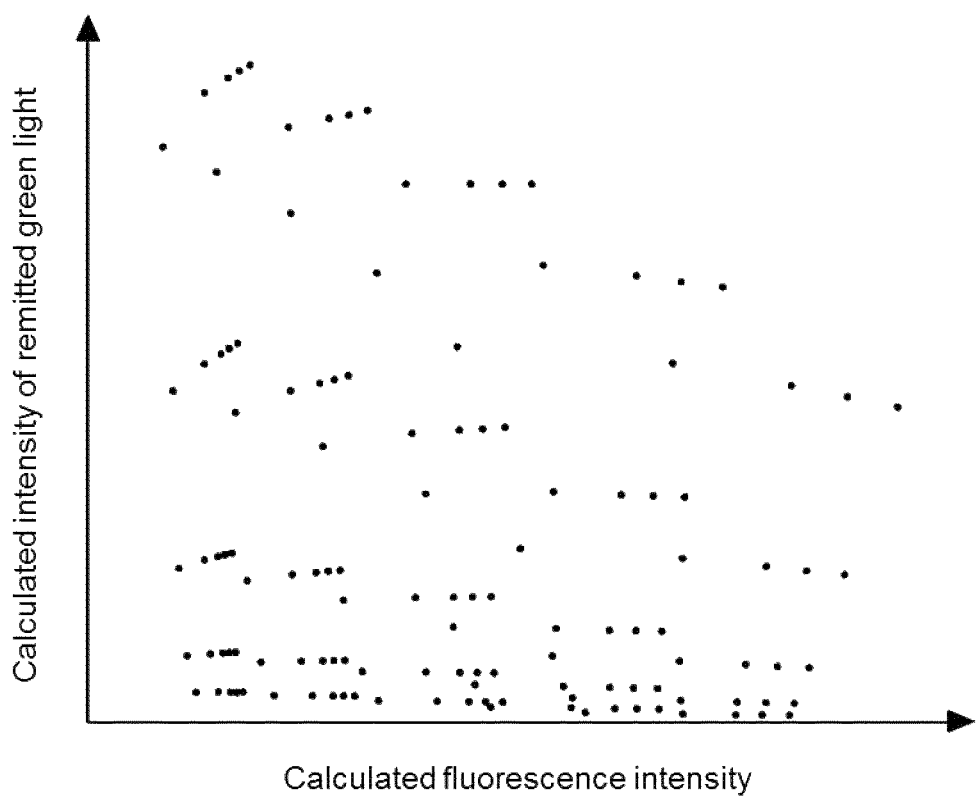
FIG. 3 is a graph showing the calculated intensity of the remitted light at a different wavelength plotted against the calculated fluorescence intensity for a Monte Carlo computer simulation.

For illustrative purposes, the results of computer simulations for idealized homogeneous tissues using a multi-fiber applicator are shown. FIG. 2 shows the calculated intensity of the remitted excitation light which is plotted against the calculated fluorescence intensity. The results of the computer simulations represents different optical parameters of the tissue (BVF between 0.25% and 8%, reduced scattering coefficient between 0.25 $mm^{-1}$ and 4 $mm^{-1}$) and epithelium layer thickness (0 µm to 400 µm). FIG. 3 shows a calculated intensity of the reflected green light (second wavelength range) which is plotted against the calculated fluorescence intensity. The results of the computer simulations represent different optical parameters of the tissue (BVF between 0.25% and 8%, reduced scattering coefficient between 0.25 $mm^{-1}$ and 4 $mm^{-1}$) and epithelium layer thickness (0 µm to 400 µm). From FIGS. 2 and 3 it can be seen, that neither remission of excitation light (425 nm) nor remission of light at the second wavelength (520 nm) individually could identify a fluorescence intensity too low for analyte measurement. Note that if each individual measurement could identify a fluorescence intensity too low for analyte measurement, a unique (for example, linear) relationship between the remitted light and the measured fluorescence light would be found. For example, all points would then lie on a straight line. FIGS. 2 and 3 show that no such relationship exists.

Nonetheless, because of high blood absorption at the excitation wavelength, the diffusely remitted excitation light strongly depends on the BVF (with less remitted light for a greater BVF), while the proportion of light remitted at the second wavelength mainly depends on light scattering and on the epithelium layer thickness (stronger scattering or thicker epithelium lead to more remitted light). Therefore, the ratio of the diffusely remitted excitation light to the power of 0.8 (the exponent is device and fiber applicator dependent) to the diffusely remitted light at the second wavelength correlates with the measured fluorescence intensity, as shown in FIG. 4.

Figure 4:
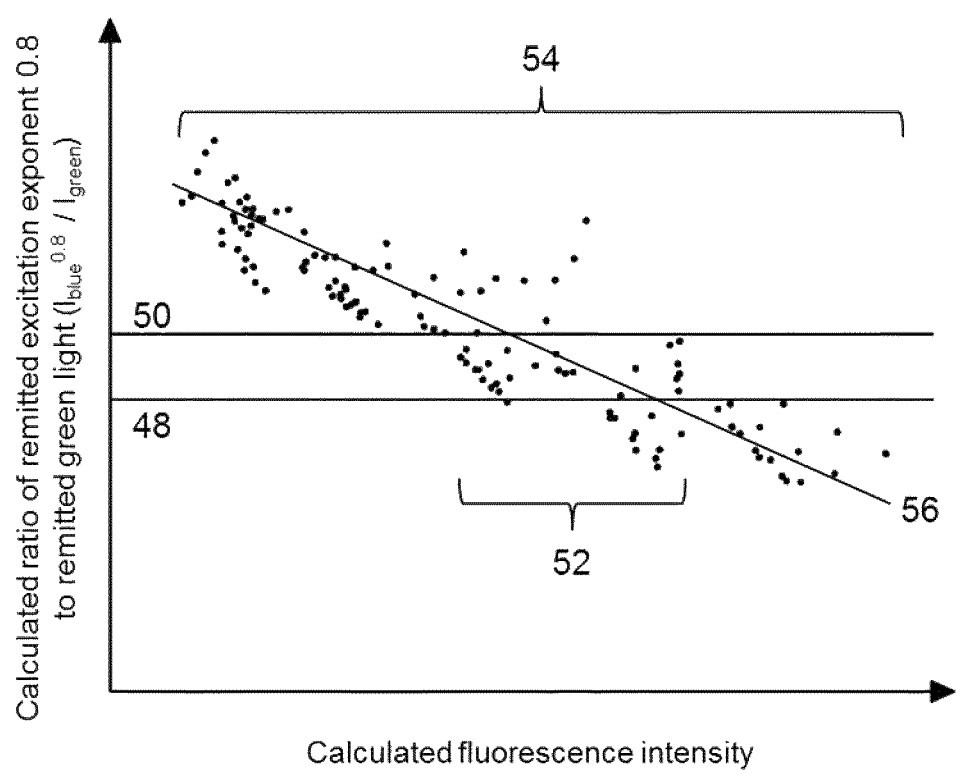
FIG. 4 is a graph showing the calculated measure derived from the remitted excitation light and the remitted light at the second wavelength plotted against the calculated fluorescence intensity for a Monte Carlo computer simulation.

FIG. 4 shows the calculated ratio of remitted excitation light to the power of 0.8 to remitted green light ($I_{blue}^{0.8}/I_{green}$) as a result of computer simulations for different optical parameters of the tissue (BVF between 0.25% and 8%, reduced scattering coefficient between 0.25 $mm^{-1}$ and 4 $mm^{-1}$) and epithelium layer thickness (0 µm to 400 µm).

By using lower and upper thresholds, 48 and 50, unfavorable measurement conditions (an excessively thick epithelial layer 38, excessive scattering, and excessively low BVF) can be identified during the measurement procedure. In the range limited by the thresholds 48 and 50, the expected measurement error 52 is significantly smaller than that for the whole measurement range 54. A quantitative evaluation of the proposed remitted light ratio also allows for the calculation of a correction factor (in this case from the slope of the regression line 56), which allows for correction of the measured fluorescence intensity to be independent of tissue optical parameters.

Tissue Autofluorescence Measurements

Tissue autofluorescence can be used to derive a measure for the BVF, the blood imprint, using the following approach. Not only is the fluorescence of the blood bound analyte (ZnPP or PP) excited, but inevitably also that of other fluorophores that are found in tissue, such as collagen or elastin, resulting in autofluorescence. The autofluorescence light propagates through the tissue until it reaches the detector. On its propagation path, parts of the autofluorescence light are absorbed by blood, with greater absorption occurring if a greater amount of blood is present in the tissue. In addition, the absorption is strongest at the spectral positions where maxima of the blood absorption are found, e.g., around 580 nm. For this reason, the autofluorescence spectrum shows a local minimum at these spectral positions (see FIG. 5).

Figure 5:
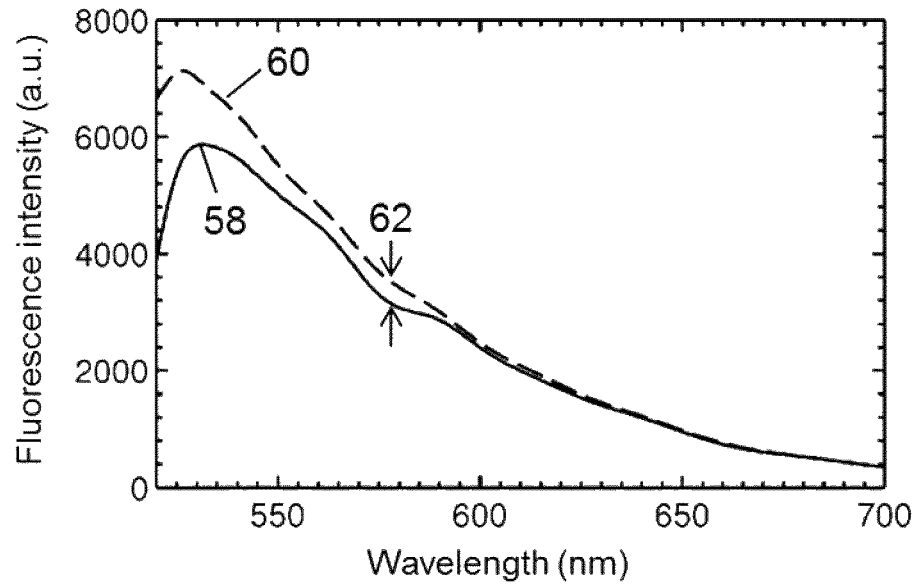
FIG. 5 illustrates a graph showing the remitted autofluorescence for tissue with large BVF (solid line) and smaller BVF (dashed line)

In FIG. 5, two autofluorescence spectra are shown measured from tissue with a large 58 and low 60 amount of blood in the measured tissue volume. The minimum 62 caused by blood absorption is evident. The quantitative evaluation of the depth of this minimum can be shown on an indicator 46 (See FIG. 12) attached to the control unit 16 giving direct feedback about the blood imprint, so that a tissue position with sufficient BVF and other tissue parameters favorable for quantitative blood analyte measurement can be found for performing a fluorescence measurement.

Figure 6:
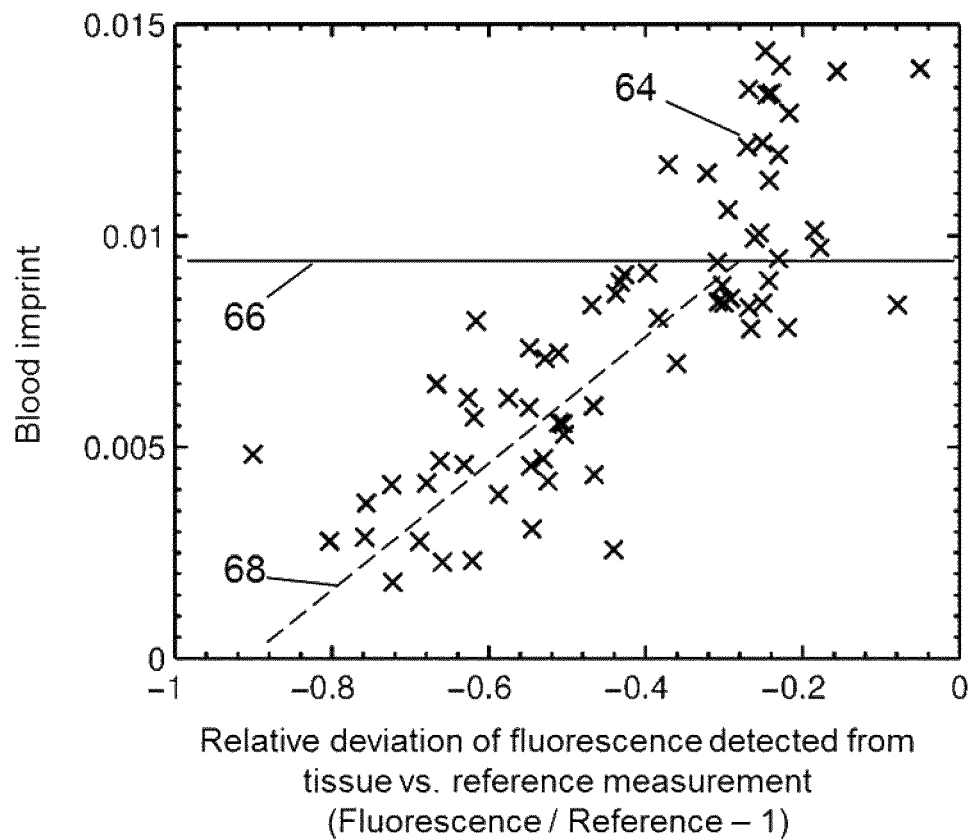
FIG. 6 is a graph showing the calculated measure for the BVF plotted against the measured relative deviation of the determined ZnPP fluorescence signal from an independent reference measurement.
Figure 7:
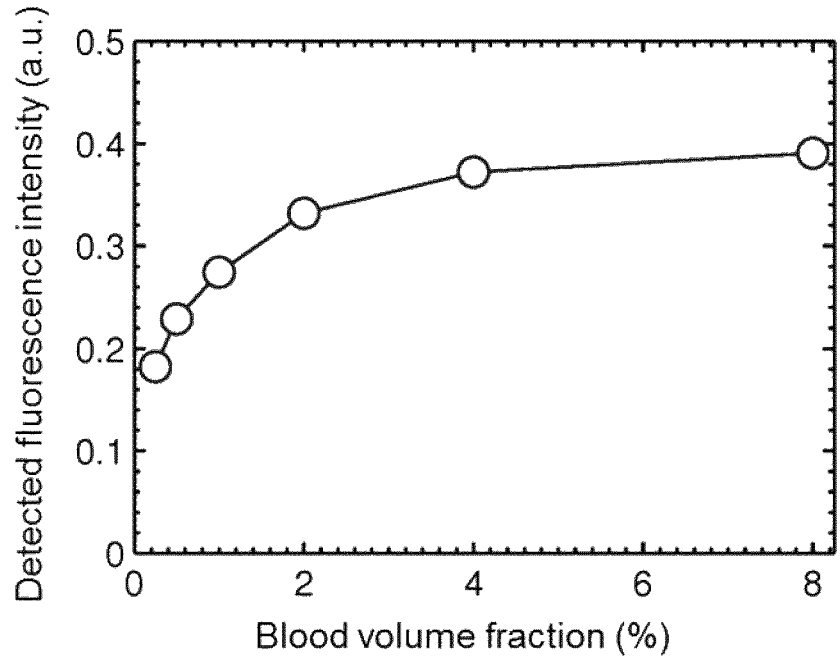
FIG. 7 is a graph showing the measured ZnPP fluorescence intensity plotted against the BVF in percent.

The problem addressed by the apparatus 10 described herein is that the measured fluorescence intensity of the analyte (ZnPP or PP) depends on the BVF as shown in FIG. 7. In FIG. 7, the measured ZnPP fluorescence intensity is plotted against the BVF for the same diluted blood sample. As the same blood sample was used, the same ratio ZnPP/heme was present for all measurements but, as shown, the measured fluorescence intensity decreases with decreasing BVF. This finding is confirmed as well for tissue measurements 64, which are shown in FIG. 6. Here, the relative deviations of the ZnPP fluorescence intensity measured in tissue from the reference value are shown. The y-axis shows the blood imprint, determined from the depth of the local minimum around 580 nm in the autofluorescence spectrum, as shown by 62 in FIG. 5. It can further be seen from FIG. 5 that below a BVF of 4% the signal decreases and therefore it does no longer allow a quantitative evaluation of the amount of ZnPP or the ZnPP/heme ratio and therefore it also provokes a false negative assessment of—for example—a iron deficiency situation. Physiologically, in tissue with good blood circulation, for example the lip, where BVFs of 1-6% would be expected, there exists the risk of performing the measurement under insufficient conditions. This could be avoided by using the inventive apparatus and method.

As can be seen from FIG. 6, the (negative relative) deviations are large for a small blood imprint (points in the lower left part of FIG. 6). However, above the threshold 66, the deviations between tissue measurement and reference value are small. Below this threshold 66, the points seem to scatter around a linear regression line 68. Based on the blood imprint determined from the autofluorescence spectrum, a determination can be made whether the ZnPP or PP fluorescence intensity will provide a quantitative measure for the ratios ZnPP/heme or PP/heme, respectively (i.e., if the blood imprint is higher than a predetermined threshold).

Alternatively, the measured fluorescence intensity may be corrected using a predetermined function such as a linear correction function, so that the corrected fluorescence intensity is then a quantitative measure for the ratios ZnPP/heme or PP/heme, respectively. As another option, the blood imprint is determined continuously by continuously acquiring autofluorescence spectra, so that the position on the tissue is repeatedly changed until the blood imprint suits the requirement that the measured ZnPP or PP fluorescence intensity provides a quantitative measure for the ratios ZnPP/heme or PP/heme, respectively.

Remission and Tissue Autofluorescence Measurements

Using either or a combination of the two approaches discussed above, information about the tissue properties can be gained.

Testing

Figure 8:
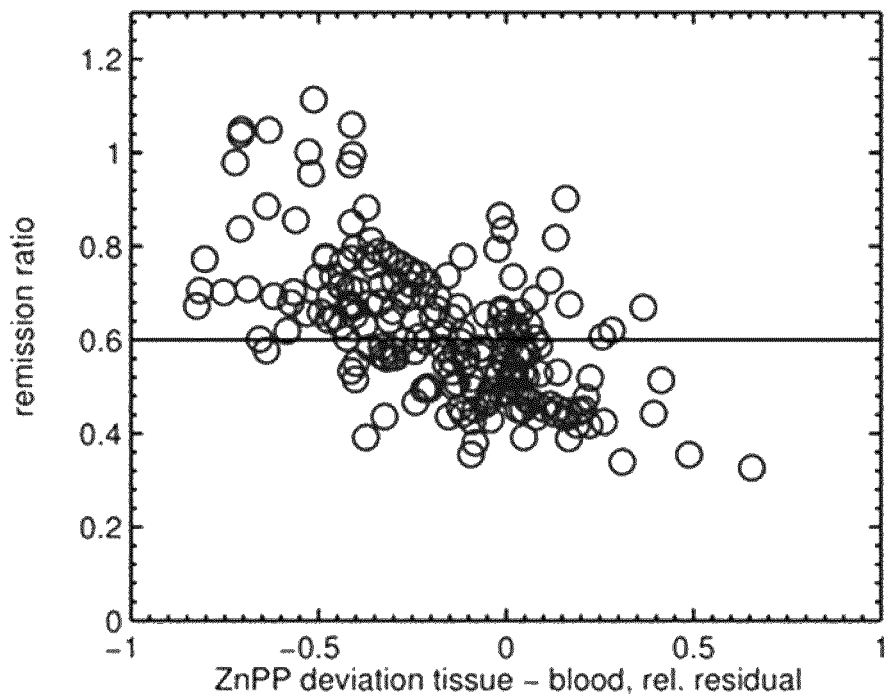
FIG. 8 is a graph showing the relative deviation between the ZnPP fluorescence measured from tissue and the ZnPP fluorescence measured from blood (ZnPP tissue minus ZnPP blood divided by ZnPP blood) compared with the "remission ratio" (the calculated measure derived from the remitted excitation light and the remitted light at the second wavelength)

For 20 subjects, the "remission ratio" (e.g., the ratio of remitted light at 425 nm to the power of 1.2 and remitted light at 520 nm) was measured at the lower lip, as well as the zinc protoporphyrin (ZnPP) fluorescence. In addition, the "real" ZnPP value was measured from the same subjects' blood samples. The relative deviation between both values (ZnPP tissue minus ZnPP blood divided by ZnPP blood) was compared with the remission ratio (0 deviation means perfect agreement) as illustrated in FIG. 8. For each subject, 10 data points exist (10 different locations on the lower lip). A threshold of 0.6 (black horizontal line) was introduced. All data points below that threshold are defined as valid.

Figure 9:
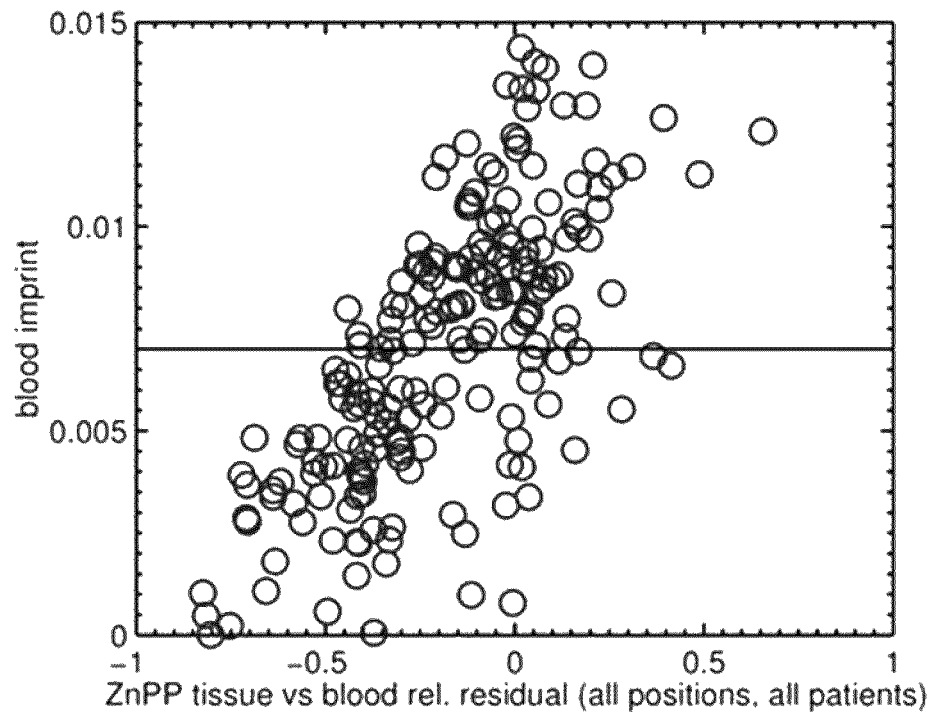
FIG. 9 is a graph showing the relative deviation between the ZnPP fluorescence measured from tissue and the ZnPP fluorescence measured from blood (ZnPP tissue minus ZnPP blood divided by ZnPP blood) compared with the "blood imprint" (fit amplitude of the blood absorption spectrum fitted to the autofluorescence spectrum measured for 425 nm excitation)

As illustrated in FIG. 9, the same was done for the blood imprint (blood absorption spectrum fitted to the autofluorescence spectrum measured for 425 nm excitation). Again, 20 subjects, 10 locations on the lower lip, each. Here, the threshold was set to 0.007; all points above would be considered as valid.

Figure 10:
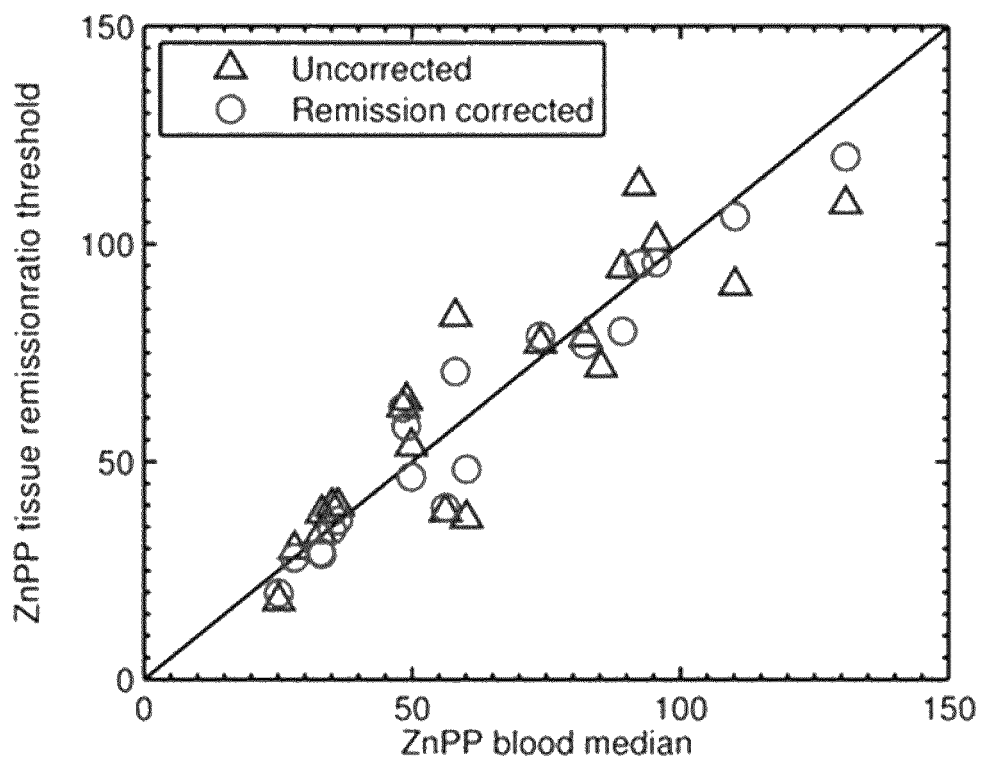
FIG. 10 is a graph showing the median ZnPP fluorescence values measured in tissue for 20 subjects, compared with the ZnPP fluorescence values measured in blood, for the uncorrected values and for the values corrected by remission measurements.

As illustrated in FIG. 10, the median ZnPP tissue value for each subject was compared with the values measured in blood, for the uncorrected values (using all measured spectra, triangles) and for the remission corrected values (using only spectra where the remission ratio is above the threshold of 0.6, circles). The Pearson correlation coefficient increases from 0.89 for the uncorrected values to 0.95 for the remission corrected values.

Figure 11:
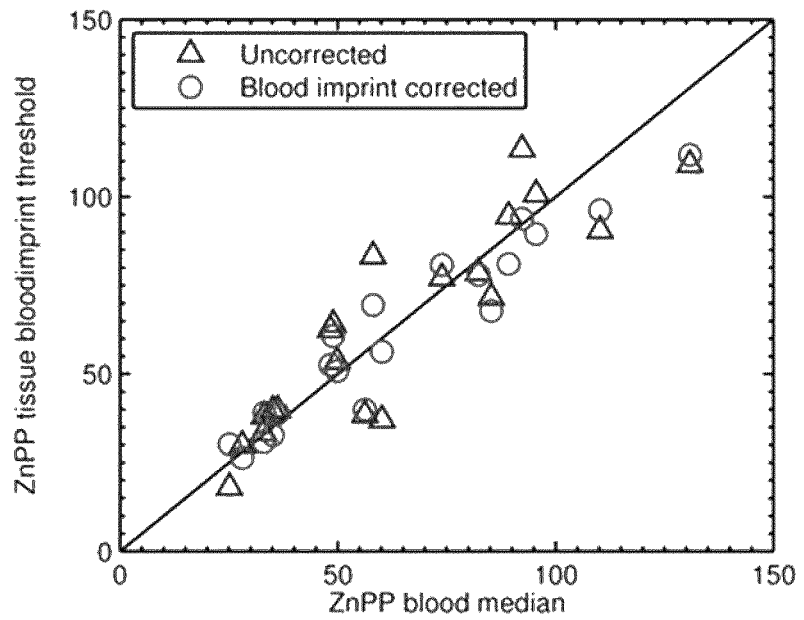
FIG. 11 is a graph showing the median ZnPP fluorescence values measured in tissue for 20 subjects, compared with the ZnPP fluorescence values measured in blood, for the uncorrected values and for the values corrected by the blood imprint.

The same was done using the blood imprint threshold (FIG. 11). Here, the Pearson correlation coefficient increases to 0.96 for the corrected spectra.

For quantitative comparison of the methods, the respective limits of agreement were calculated, see Table 1 below. This shows that both correction methods work, with the correction by blood imprint being slightly better.

TABLE 1

| Limits of Agreement with confident intervals for the different correlations (smaller is better) | | | |
|---|---|---|---|
| Limits of Agreement | LoA | 2.5% | 97.5% |
| 1  Blood vs. tissue uncorrected | 28.1 | 22.0 | 37.1 |
| 2  Blood vs. remission corrected | 19.1 | 13.4 | 26.2 |
| 3  Blood vs. blood imprint corrected | 17.1 | 13.0 | 22.6 |

Several embodiments of a probe 22 as a part of the apparatus 10 are shown in FIGS. 12 to 19.

Figure 12:
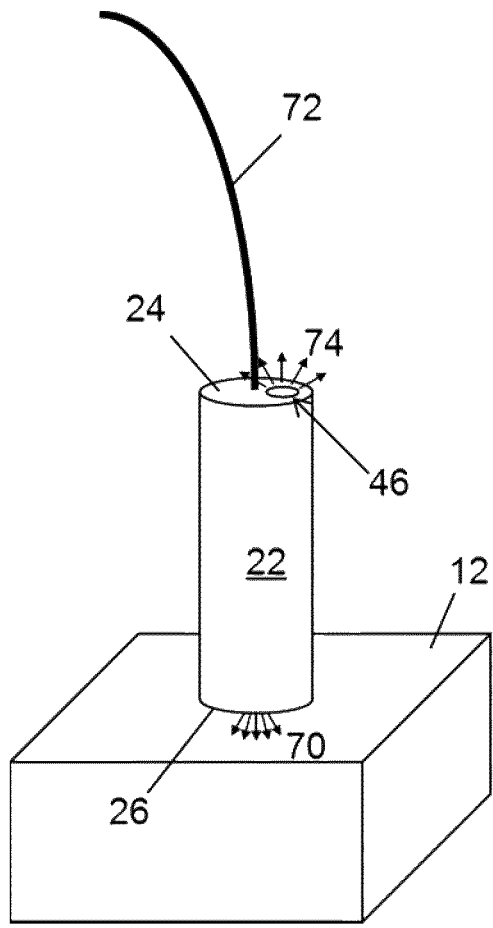
FIG. 12 is a schematic illustration of a probe of the inventive apparatus according to one embodiment of the invention.

FIG. 12 shows a schematic illustration of parts of the detection unit 16 configured as a probe 22 of the inventive apparatus according to a first embodiment. The probe 22 has a proximal end 24 and a distal end 26, wherein the distal end 26 is configured to be applied directly or indirectly to the tissue 12. It can be seen that probe 22 further comprises an indicator 46, which shows the degree of deviation from a satisfactory blood imprint and/or optical parameters such as inappropriate epithelium thickness or scattering. The indicator 46 may be a display on a computer or a smart phone screen or can be attached to an optical fiber or an optical fiber probe. In FIG. 12, a schematic of this indicator 46 is shown, which is embedded into the fiber optic probe applicator 22. The indicator 46 can be controlled by an electrical wire or optical fiber that is guided to the probe 46 in parallel to the optical fiber bundle 72 that is used to guide excitation light 70 and fluorescence light for the measurement on tissue 12. The indicator 46 may use LEDs or other light sources to indicate the deviation of the blood imprint and/or tissue parameters by colored light 74. This may be realized in a manner comparable to a traffic light, showing green light, if a reliable measurement of the ZnPP/heme or PP/heme can be done at the probed site, orange light for acceptable reliability and red light for an unreliable measurement. The indicator 46 can also be realized as sound where its frequency or volume indicates the deviation from a satisfactory blood imprint and/or tissue parameters. It may also be realized as a vibrator, e.g. integrated in the probe's applicator.

Figure 13:
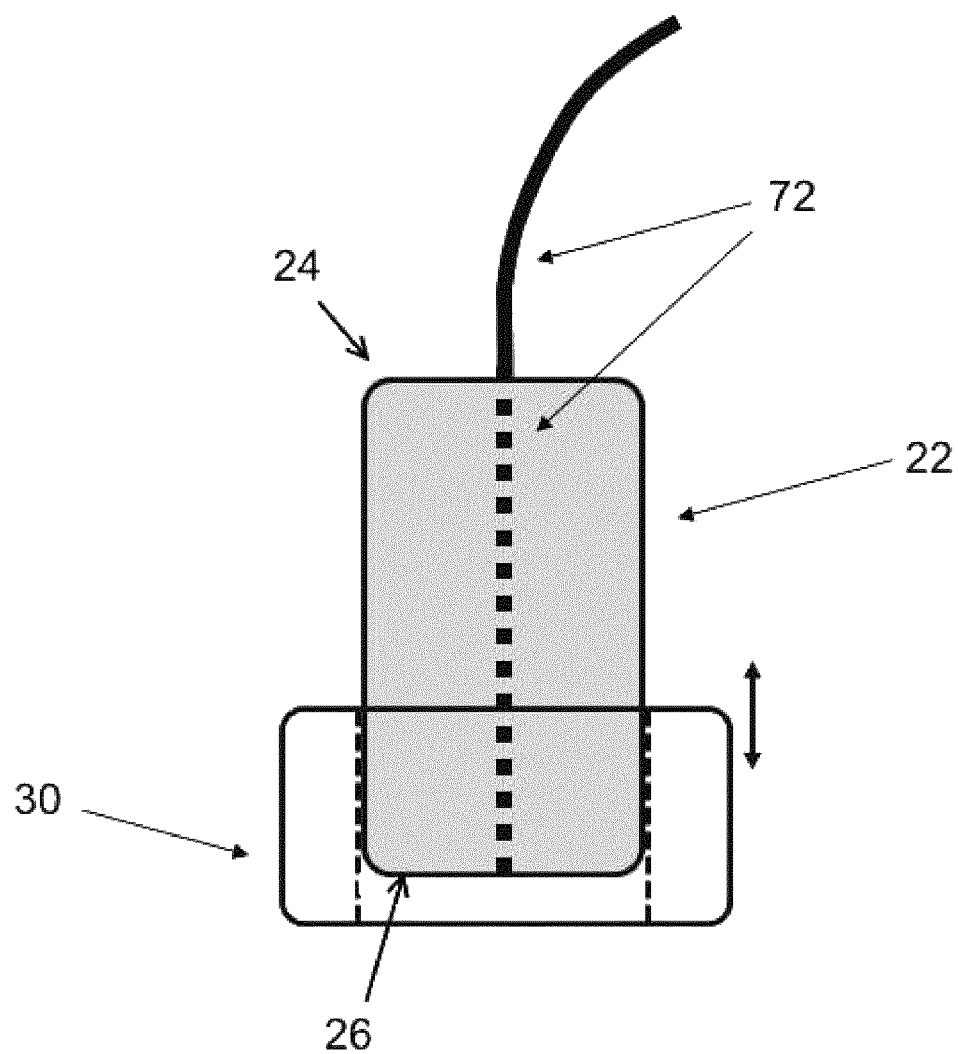
FIG. 13 is a schematic illustration of a probe of the inventive apparatus according to another embodiment of the invention.

FIG. 13 shows a further embodiment of parts of the detection unit 16 configured as a probe 22. The probe 22 comprises a cover 30 attached to the distal end 26. According to the present embodiment the cover 30 is slidably attached to the probe 22 at the distal end 26.

FIGS. 14 to 19 show further embodiments of parts of the detection unit 16 configured as a probe 22. The probes 22 according to the embodiments shown in FIGS. 14 to 19 each comprise at least one suction aperture 28 formed at the distal end 26 of the probe 22 or a suction aperture 28 is formed within the cover 30, wherein the suction aperture 28 is configured to be applied directly or indirectly to the tissue 12.

Figure 14:
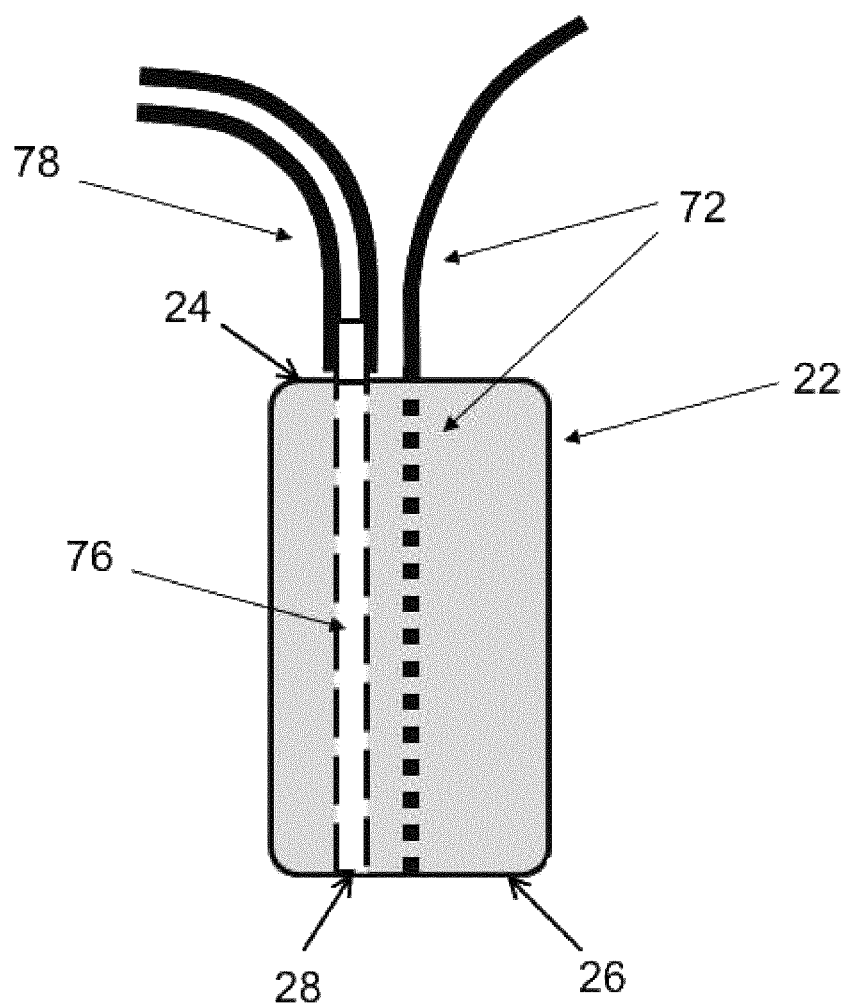
FIG. 14 is a schematic illustration of a probe of the inventive apparatus according to another embodiment of the invention.
Figure 15:
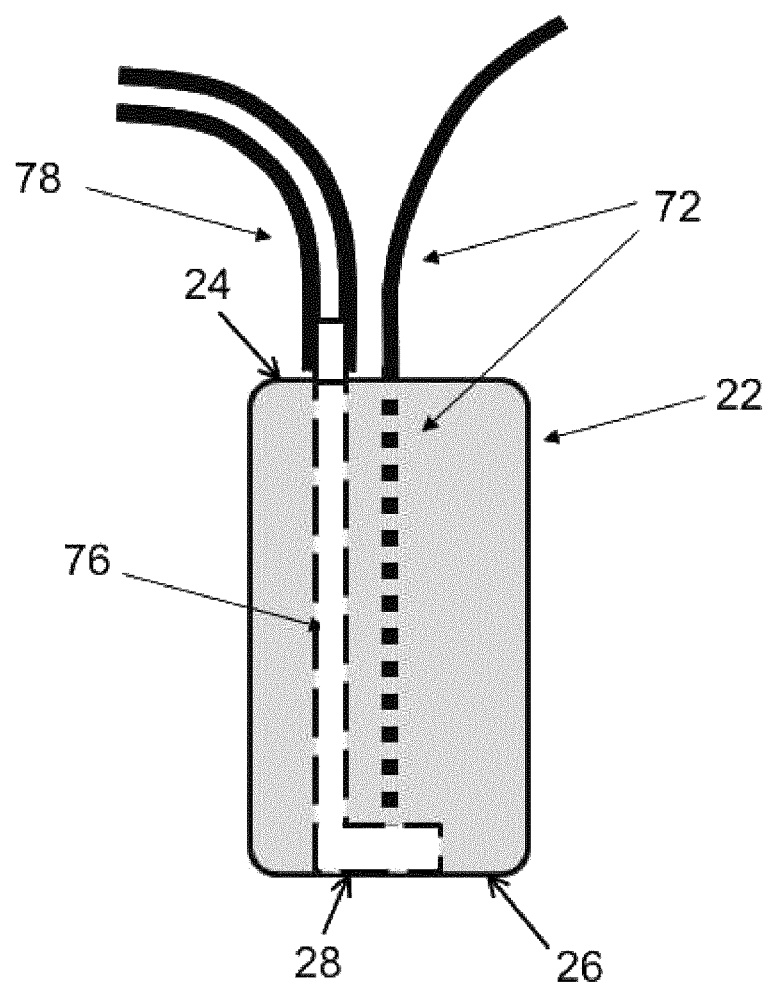
FIG. 15 is a schematic illustration of a probe of the inventive apparatus according to another embodiment of the invention.
Figure 16:
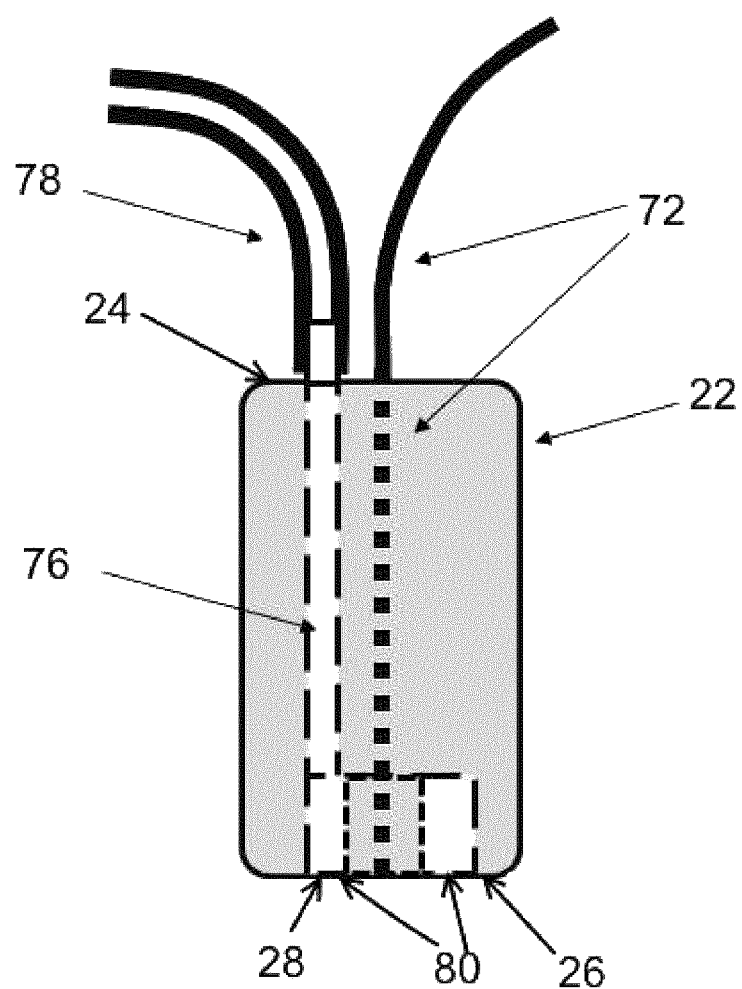
FIG. 16 is a schematic illustration of a probe of the inventive apparatus according to another embodiment of the invention.
Figure 17:
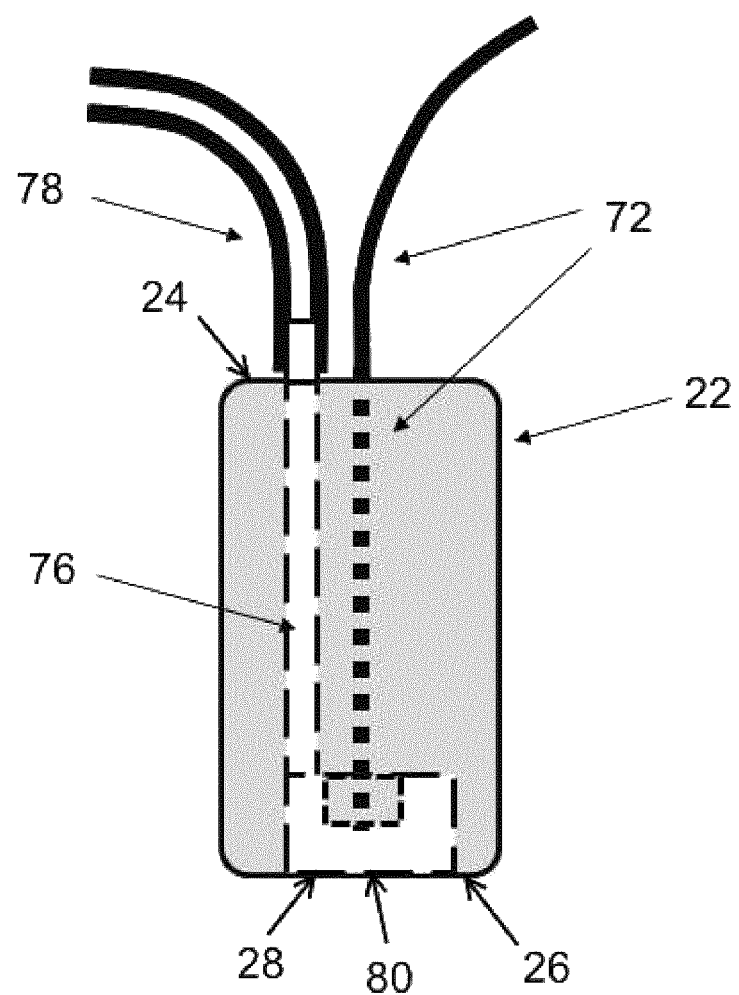
FIG. 17 is a schematic illustration of a probe of the inventive apparatus according to another embodiment of the invention.
Figure 18:
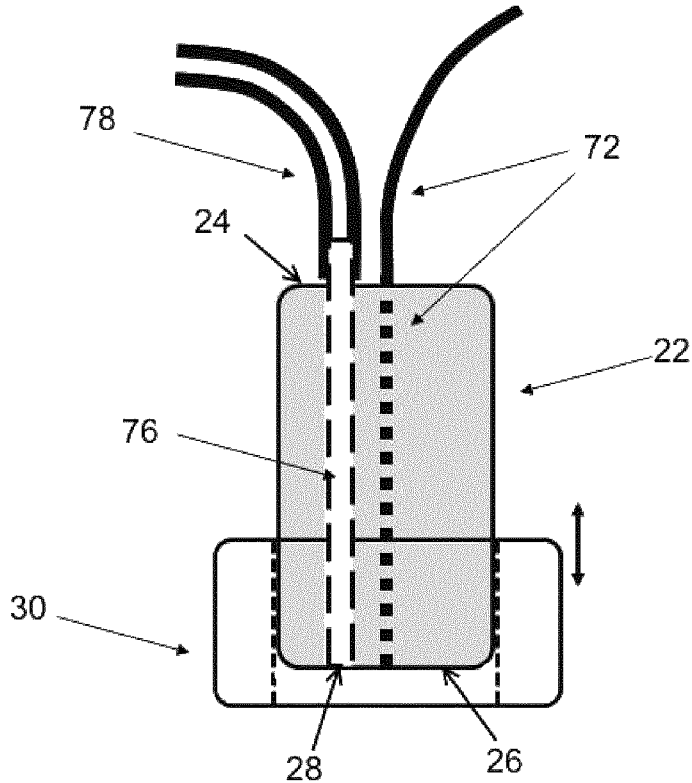
FIG. 18 is a schematic illustration of a probe of the inventive apparatus according to another embodiment of the invention.
Figure 19:
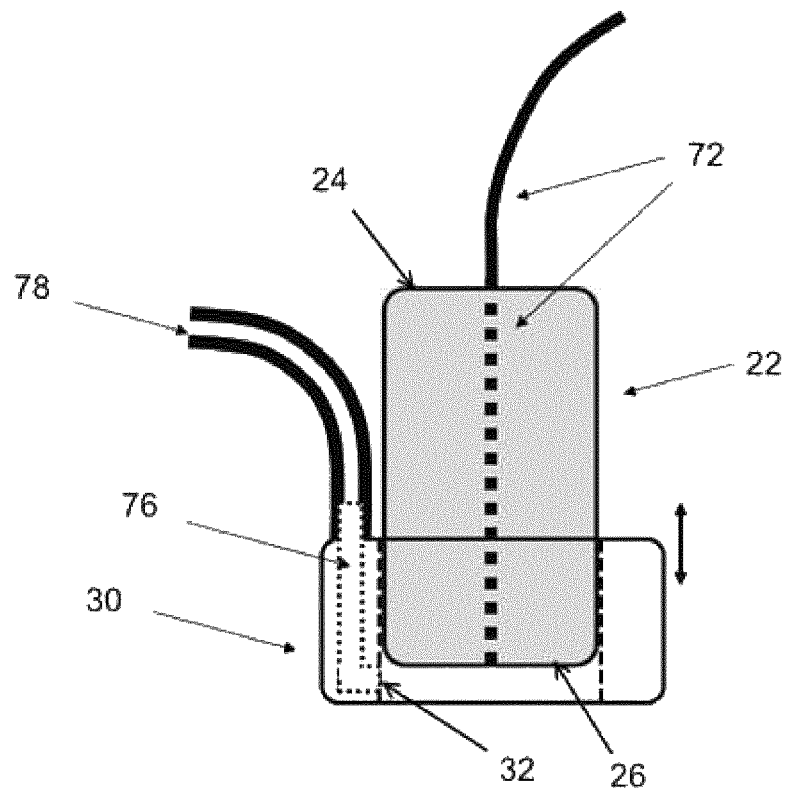
FIG. 19 is a schematic illustration of a probe of the inventive apparatus according to another embodiment of the invention.

FIG. 14 shows a first embodiment of the probe 22 comprising said suction aperture 28. The probe 22 contains the fiber optic for fluorescence excitation and fluorescence detection. The fiber optic can be designed as a single optical fiber or an optical fiber bundle 72. The fiber bundle 72 comprising a single way or separate ways for the excitation light and the detection light. By means of the optical fiber or optical fibers 72 remission light after multiple scattering in the tissue 12 can be detected at any wavelengths. An increase of the BVF is achieved by suction of the tissue 12 which is in contact with the distal end 26 of the probe 22. For this purpose, a suction channel 76 ending at the suction aperture 28 is arranged next to the measuring site under the optical fiber or the optical fibers 72. Low pressure or a vacuum can be generated by a suction pump (not shown) connected via a hose connection 78 to the suction channel 76. By means of the low pressure or vacuum under the suction channel 76 erythrocytes in the nearby tissue are concentrated and therefore the BVF is increased. This can be seen and controlled on the basis of the spectral signature of the absorption of oxygenated blood in the fluorescence emission spectrum at a minimum of about 580 nm.

FIGS. 15 to 19 show further embodiments of the probes comprising at least one suction aperture 28 formed at the distal end 26 of the probe 22 or a suction aperture 32 formed in the cover 30. Due to this, the low pressure or vacuum can be generated by guiding the probe 22 as a piston within a hermetically sealed cover 30 (see FIG. 18). For this purpose, first the cover 30 and the probe 22 are both placed in a flush fitting mode on the surface of the tissue 12 and then the distal end 26 of the probe 22 is slightly pulled back. The suction effect can be increased, if applicable, by a suction means attached to or within to the probe 22 (see FIGS. 15 to 17) or within the cover 30 (see FIG. 19) comprising the suction channel 76 connected via the hose connection 78 to the suction pump (not shown). For a better expansion of the suction effect to the area under the measuring volume, several suction channels (not shown) or an annular shape 80 of the suction channel 72 can be provided at the distal end 26 of the probe 22 (see FIGS. 16 and 17). Further, the distal fiber end can be arranged with a variable distance to the surface of the tissue 12 (see FIGS. 15, and 17 to 19).

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. An apparatus for reliable quantitative measurement of a fluorescent blood analyte in tissue comprising:
   at least one light source for emitting excitation light at a first wavelength range between 350 nm and 450 nm to the tissue; or
   at least one light source for emitting excitation light at a first wavelength range between 350 nm and 450 nm and light at a second wavelength or wavelength range between 455 nm and 750 nm where blood absorption is smaller to the tissue;
   a detection unit for measuring:
      a) a portion of fluorescent light emitted by the fluorescent blood analyte excited by illumination of the tissue with light in the first wavelength range, and at least one of
      b) a portion of auto fluorescence emitted by the tissue at a wavelength range between 530 and 600 nm, or
      c) a portion of remitted excitation light at the first wavelength range and a portion of remitted light at the second wavelength range;
   a control unit, the control unit operating the light source and detection unit; and
   a processor configured to:
      determine a first parameter from at least one intensity of the portion of the auto fluorescence emitted by the tissue at a wavelength range between 530 and 600 nm and identify measurements or tissue sites where a detected amount of fluorescent light is a quantitative measure of the fluorescent blood analyte based on a comparison of the first parameter with a predetermined threshold, or
      determine a second parameter from the remitted excitation light at the first wavelength range and the remitted light at the second wavelength range and identify measurements or tissue sites where a detected amount of fluorescent light is a quantitative measure of the fluorescent blood analyte based on a comparison of the second parameter with a predetermined threshold,
   wherein the second parameter is a ratio of the remitted excitation light at the first wavelength range to the remitted light at the second wavelength range to identify measurements or tissue sites, or
   wherein the second parameter is a ratio of the remitted excitation light at the first wavelength range to the remitted light at the second wavelength range to derive a correction factor based on the second parameter and to scale a measured fluorescence intensity based on the correction factor to provide a quantitative measure of the fluorescent blood analyte.

2. The apparatus according to claim 1, wherein the at least one light source and the detection unit are configured as a single integral component.

3. The apparatus according to claim 1, wherein the detection unit comprises optical means for collecting emitted fluorescent light, the remitted excitation light at the first wavelength range, and the remitted light at the second wavelength range.

4. The apparatus according to claim 1, wherein the detection unit comprises a probe having a proximal end and a distal end, wherein the distal end is configured to be applied directly or indirectly to the tissue.

5. The method according to claim 1, wherein a wavelength of the auto fluorescence emitted by the tissue is 580 nm.

6. The apparatus according to claim 4, wherein said probe further comprises at least one suction means formed at the distal end of the probe.

7. The apparatus according to claim 6, wherein said suction means comprising at least one suction aperture formed at the distal end of the probe.

8. The apparatus according to claim 4, wherein said probe further comprises a cover attached to the distal end, wherein the cover is configured to be applied directly or indirectly to the tissue.

9. The apparatus according to claim 8, wherein the at least one suction means is formed within the cover.

10. The apparatus according to claim 1, wherein the detection unit is configured as a handheld device.

11. The apparatus according to claim 1, wherein the apparatus comprises a light guide guiding excitation light to the tissue or for collecting emitted fluorescent light, the remitted excitation light at the first wavelength range, or the remitted light at the second wavelength range.

12. The apparatus according to claim 11, wherein the light guide is an optical fiber or fiber bundle.

13. The apparatus according to claim 1, wherein the fluorescent blood analyte measured includes at least one of a zinc protoporphyrin (ZnPP)/heme, protoporphyrin IX (PP)/heme ratios, ZnPP, or PP concentrations.

14. The apparatus according to claim 1, wherein a wavelength of the auto fluorescence emitted by the tissue is 580 nm.

15. The apparatus according to claim 1, wherein the processor is further configured to derive a correction factor based on the at least one intensity of the portion of the auto fluorescence emitted by the tissue at the wavelength range between 530 and 600 nm and to scale a measured fluorescence intensity based on the correction factor to provide a quantitative measure of the fluorescent blood analyte.

16. The apparatus according to claim 1, wherein the processor is configured to estimate a blood volume fraction from the auto fluorescence emitted by the tissue.

17. A method of measuring quantitatively a fluorescent blood analyte in tissue comprising:
    emitting excitation light at a first wavelength range between 350 nm and 450 nm to the tissue; or
    emitting excitation light at a first wavelength range between 350 nm and 450 nm and light at a second wavelength or wavelength range between 455 nm and 750 nm where blood absorption is smaller to the tissue;
    detecting a portion of the fluorescent light emitted by the fluorescent blood analyte excited at the first wavelength range;
    detecting at least one of:
        a portion of auto fluorescence emitted by the tissue at a wavelength range between 530 and 600 nm or
        detecting a portion of remitted excitation light at the first wavelength range and a portion of the remitted light at a second wavelength range; and
    determining a least one of:
        a first parameter based on at least one intensity of the portion of the auto fluorescence emitted by the tissue at a wavelength range between 530 and 600 nm based on a comparison of the first parameter with a predetermined threshold, or
        a second parameter based on a detected intensity of the remitted excitation light at the first wavelength range and a detected intensity of the remitted light at the second wavelength range, and a comparison of the second parameter with a predetermined threshold,
    deriving a correction factor based on the second parameter and scaling the measured fluorescence intensity as a quantitative measure of the blood analyte, or
    wherein the second parameter is a ratio of the remitted excitation light at the first wavelength range to the remitted light at the second wavelength range to derive a correction factor based on the second parameter and to scale a measured fluorescence intensity based on the correction factor to provide a quantitative measure of the fluorescent blood analyte.

18. The method according to claim 17, further comprising:
    determining an estimated blood volume fraction from the auto fluorescence emitted by the tissue, excluding measurements or tissue sites unsuitable for reliable quantitative determination of the blood analyte.

19. The method according to claim 17, further comprising:
    determining an estimated blood volume fraction from the second parameter, wherein the second parameter is a ratio of the detected intensity of the remitted excitation light at the first wavelength range and the detected intensity of the remitted light at the second wavelength range, excluding measurements or tissue sites unsuitable for reliable quantitative determination of the blood analyte; or a ratio of the detected intensity of the remitted light at the second wavelength range and the detected intensity of the remitted excitation light at the first wavelength range,
    excluding measurements or tissue sites unsuitable for reliable quantitative determination of the blood analyte.

20. The method according to claim 17, further comprising:
    deriving a correction factor based on the at least one intensity of the portion of auto fluorescence portion emitted by the tissue at a wavelength range between 530 and 600 nm and scaling a measured fluorescence intensity as a quantitative measure of the blood analyte.

21. The method according to claim 17, wherein the first parameter or the second parameter comprises information that determines influence on a fluorescence intensity by a tissue structure.

22. The method according to claim 21, wherein the information comprises a thickness of a superficial tissue layer.

23. The method according to claim 17, wherein the first parameter or the second parameter comprises information that determines influence on a fluorescence intensity by optical parameters.

24. The method according to claim 17, further comprising:
    increasing a blood volume fraction by sucking via a suction device at least a part of the tissue where the excitation light at the first wavelength range is emitted.

25. The method according to claim 17, wherein the fluorescent blood analyte measured includes at least one of a zinc protoporphyrin (ZnPP)/heme, protoporphyrin IX (PP)/heme ratios, ZnPP, or PP concentrations.

* * * * *